United States Patent [19]

Kudla

[11] 4,279,901

[45] Jul. 21, 1981

[54] TOPICAL OINTMENT

[75] Inventor: Ronald M. Kudla, New York, N.Y.

[73] Assignee: American Cyanamid Company, Stamford, Conn.

[21] Appl. No.: 109,017

[22] Filed: Dec. 31, 1979

[51] Int. Cl.³ .............................................. A61K 31/58
[52] U.S. Cl. ........................... 424/241; 260/239.55 D; 424/238; 424/243
[58] Field of Search ......................... 424/238, 241, 243

[56] References Cited

U.S. PATENT DOCUMENTS 3,924,004  12/1975  Chang et al. .......................... 424/241

*Primary Examiner*—Elbert L. Roberts
*Attorney, Agent, or Firm*—Robert P. Raymond

[57] ABSTRACT

Non-oxidizing, non-peroxide forming, non-aqueous vehicle for topical application of medicaments comprising ethylene carbonate and a non-aqueous petroleum wax component such as polawax or petrolatum.

1 Claim, No Drawings

TOPICAL OINTMENT

BACKGROUND OF THE INVENTION

This invention relates to vehicles for topical application of medicaments. In particular, this invention relates to new, improved medicament vehicles having advantages over previously known vehicles.

One of the oldest types of medicament vehicles is the ointment; a preparation containing active medications that can be readily applied and rubbed into the skin. It serves as a means for distributing the medication uniformly over the skin surface and maintaining it there until beneficial action can occur. The earliest ointment preparations were based on fats, waxes, greases and petrolatum. These are, by nature, greasy, or not water-washable and having a limited ability to release medication to the skin. A non-aqueous ointment of more recent origin is a mixture of polyethylene glycols having molecular weights of 1,000 to 20,000. This vehicle, although water-washable, has a greasy texture and does not provide an occlusive dressing on a treated surface. Prior to this invention, these anhydrous ointment bases were the only vehicles available for medicaments which deteriorated in the presence of moisture, oxidants, and peroxides.

Emulsified creams, such as cold creams, were developed to reduce greasiness, while still maintaining the unctuousness and spreadability of the older greasy-type ointments. The emulsified creams have an aqueous base, however, and are not suitable for many drugs because their water content does not provide an appropriate milieu for optimum stability. The medicament in turn may destroy the emulsions, that is, break the emulsions and permit separation of the vehicle components.

One system which is not subject to the above disadvantages is the non-aqueous fatty alcohol-propylene glycol vehicle described in U.S. Pat. No. 3,592,930 granted to Katz et al. Another system is an improved non-aqueous vehicle with a propylene carbonate solvent system, U.S. Pat. No. 3,924,004 granted to Chang et al, as well as U.S. Pat. No. 4,017,615 granted to Shastri, et al.

A problem created by these formulae is the presence of glycol with its potential for peroxide formation. A recent study has indicated that peroxidation of the medicament vehicle may adversely affect the medicament (Implications of Peroxide Formation in Lotion and Ointment Dosage Forms Containing Polyethylene Glycols, McGinty et al. *Drug Development Communications*, 2(6), 505–519 (1976)).

The mechanisms of degradation may be depicted thus:

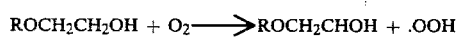  (1)

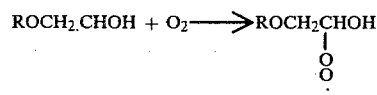  (2)

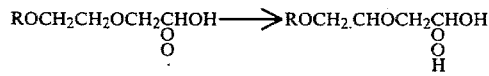  (3)

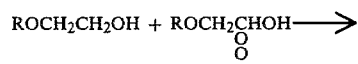  (4)

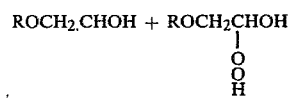

A markedly superior medicament vehicle would arise if the potential for peroxide formation and actual peroxide formation were severly limited.

Such vehicle should retain the properties of a non-aqeuous phase that was nevertheless unusable as to a second non-aqueous phase. This would allow substances such as corticosteroids to remain available in relatively high concentrations in one phase and not be distributed throughout the second phase. Such vehicle should form an occlusive seal as to air yet permit mobilization of aqueous soluble materials.

It is accordingly the purpose of this invention to retain the advantages of the previous non-aqeuous biphasic type ointments while avoiding the problems attendant to peroxide formation present in the prior art.

It is a further object of this invention to provide a vehicle using a particular solvent, as to topical preparations. Ethylene carbonate has exceptional solubilizing properties, particularly for corticosteroids. By combining surfactant with a petroleum wax type base, an antioxidant and propylene carbonate, a stable cream can be prepared.

SUMMARY OF THE INVENTION

The invention, which is an improvement over the prior art, is a non-oxidizing, non-peroxide forming non-aqeuous vehicle for topical application of medicaments. Ethylene carbonates and a petroleum wax form the base of the vehicle which may also include small amounts of anti-oxidants such as Tenox II ® (Eastman Chemical Products), tocopherol, and an acidifying agent such as lactic acid. The resultant vehicle is particularly suitable as a vehicle for the application of steroidal agents.

DETAILED DESCRIPTION OF THE INVENTION

The vehicle for medicaments of this invention principally relates to ointments containing stable and clinically effective steroids and the vehicle characterized by the incorporation of propylene carbonates.

More particularly, steroids of the class of adreno corticosteroids and synthetic analogues exhibiting anti-inflammatory properties are most useful with the ointment vehicle of this invention.

This invention, in particular, relates to an ointment containing Amcinonide ®, a steroidal agent of the formula 16α,17α-cyclo-pentylidenedioxy-9α-fluoro-11β,21-dihydroxy-1,4-pregnadiene-3,20-dione 21-acetate, as an active medicament.

This invention indicates that sufficient stability is obtained by incorporating ethylene carbonate singly in vehicle ingredients commonly used, and, if desired, antioxidants and/or organic acids.

Ethylene carbonate is of the formula: is of the formula:

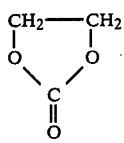

Other exemplary organic acids are boric acid, tartaric acid and malic acid. Antioxidants may be desired especially in the case in which the petrolatum base bears peroxide contaminants.

To maintain a high concentration of steroid in the carbonate phase, the carbonate should be present from about 0.01% to about 10% by weight. As it is impossible to predict the medicament requirements of any specific physiologic condition being treated, one may exceed these limits in any specific therapeutic formulation, depending on the subject and the active agent, limited only by toxicity and solubility. These considerations would similarly determine the percentage of medicament added.

An optimum amount of ethylene carbonate is from 0.05 to 5 weight percent, and for Amcinonide ® ointment in particular, preferably from 1 to 2 weight percent.

As an antioxidant, tocopherol or Tenox II ® is specified, and lactic acid can be used for the organic acid. Some embodiments may use lactic acid or other organic acid to adjust pH. The optimum amount of lactic acid is 0.01 weight percent or below, preferably approximately 0.005 weight percent. In using tocopherol or Tenox II ® as an antioxidant in the ointment containing Amcinonide ® relating to this invention, the optimum weight percent of tocopherol or Tenox II ® is from 0.01 to 1, preferably from 0.02 to 0.7.

As other ingredients of the vehicle, commonly used polawax, white petrolatum, etc., can be used in an appropriate amount. Polawax is also designated Emulsifying Wax N.F.

Clinically effective doses and dosage of Amcinonide ® ointment relating to this invention are similar to those of conventional other topical corticosteroids; that is, an optimum amount of this ointment shall be applied to the site of disease, and if required, with occlusive dressing.

The process of manufacture of steroidal ointment relating to this invention is non-limiting, but one of typical methods is as follows:

To ethylene carbonate and polawax, an antioxidant may be added; the mixture is heated to solution, to which the steroid is added, heated, mixed for solubilization, to the mixture, white petrolatum already liquefied by heating is added, heated, and mixed until homogeneity of the ingredients is obtained; then, the mixture is cooled to ambient temperature with appropriate mixing.

Following are examples to embody the process:

EXAMPLE 1

| | |
|---|---|
| Amcinonide ® | 0.105 (%) |
| Polawax | 0.750 |
| Ethylene carbonate | 1.500 |
| Tenox II ®* | .025 |
| White petrolatum | 97.620 |
| | 100.000 |

Ethylene carbonate and polawax are mixed and heated to 65°–70° C., and Amcinonide ® is dissolved in the mixture with heating. To the mixture white petrolatum already dissolved at 65°–70° C. is added, mixed at about 70° C. until homogeneity is obtained. The mixture is then cooled to about 30° C. with agitation.

EXAMPLE 2

| | |
|---|---|
| Amcinonide ® | 0.105 (%) |
| Polawax | 0.750 |
| Ethylene carbonate | 5.000 |
| Tenox II ®* | 0.025 |
| White petrolatum | 94.975 |
| | 100.000 |

To ethylene carbonate and polawax, tocopherol and Amcinonide ® are added, and the same method of Example 1.

EXAMPLE 3

| | |
|---|---|
| Amcinonide ® | 0.105 (%) |
| Polawax | 0.750 |
| Ethylene carbonate | 1.500 |
| Tocopherol | 0.500 |
| White petrolatum | 97.145 |
| | 100.000 |

The method is the same as that described in Example 2.

EXAMPLE 4

| | |
|---|---|
| Amcinonide ® | 0.105 (%) |
| Polawax | 0.750 |
| Ethylene carbonate | 1.500 |
| Tenox II ®* | 0.025 |
| White petrolatum | 97.620 |
| | 100.000 |

The method to make the ointment is the same as that described in Example 2, except that tocopherol is replaced with Tenox II ®.

EXAMPLE 5

| | |
|---|---|
| Amcinonide ® | 0.105 (%) |
| Polawax | 0.750 |
| Ethylene carbonate | 1.500 |
| Tenox II ®* | 0.025 |
| Lactic acid | 0.005 |
| White petrolatum | 97.615 |
| | 100.000 |

*Tenox II ® is a product of Eastman Chemical Products, Inc. Kingsport, Tenn., and contains 20% BHA, 6% propyl gallate, 4% citric acid, and 70% propylene glycol. The tiny resultant percentage of propylene glycol will not form sufficient peroxide to significantly affect steroid integrity and the resultant ointment is considered essentially free of components capable of peroxide formation.

The method is the same as that described in Example 4, except that lactic acid is added in solution to Tenox II ®.

EXAMPLE 6

| | |
|---|---|
| Amcinonide ® | 0.105 (%) |
| Polawax | 0.750 |
| Ethylene carbonate | 3.000 |
| White petrolatum | 96.145 |
| | 100.000 |

The method is the same as that described in Example 1.

The stability of these ointments was shown in accelerated tests of one month at room temperature, 37° C. and 45° C. with the ointments of Examples 1 and 2. No loss of homogenity was observed.

The foregoing examples include the steroid Amcinonide ®. It will be obvious to those skilled in the art that other steroids such as hydrocortisone, betamethasone, dexamethasone, flumethasone, fluorocinonide, desoximethasone, flurandrenolide, fluomethanlone, halocinide, methyl prednisolone, prednisolone, triamcinolone will also be suitable medicaments to add the ointment vehicle of the invention. In addition other suitable medicaments such as iodochlorhydroxypryin, lidocaine, pyrilamine maleate salicylic acid, allantoin, resorcinol, chlorhydroxyquinoline, zinc oxide, bufexamic acid might be added.

Other embodiments of the invention will be obvious to those skilled in the art without departing from the spirit of the invention.

The invention is limited solely by the claims.

I claim:

1. An ointment which is essentially non-oxidizing and essentially non-aqueous for topical application of medicament, such ointment comprising from 0.5 to 5 weight percent of ethylene carbonate, polawax and white petrolatum in an amount that forms a total of 100 weight percent in the presence of an active medicament wherein the active medicament is 16α,17α-cyclo-pentylidenedioxy-9α-fluoro-11α,21-dihydroxy-1,4-pregnadiene-3,20-dione-21-acetate.

* * * * *